United States Patent
Eggers et al.

(10) Patent No.: US 7,494,473 B2
(45) Date of Patent: Feb. 24, 2009

(54) ELECTRICAL APPARATUS AND SYSTEM WITH IMPROVED TISSUE CAPTURE COMPONENT

(75) Inventors: Philip E. Eggers, Dublin, OH (US); Andrew R. Eggers, Ostrander, OH (US); Eric A. Eggers, Portland, OR (US)

(73) Assignee: Intact Medical Corp., Natick, MA (US)

( * ) Notice: Subject to any disclaimer, the term of this patent is extended or adjusted under 35 U.S.C. 154(b) by 612 days.

(21) Appl. No.: 10/730,633

(22) Filed: Dec. 8, 2003

(65) Prior Publication Data

US 2005/0124915 A1 Jun. 9, 2005

Related U.S. Application Data

(63) Continuation-in-part of application No. 10/630,336, filed on Jul. 30, 2003, now Pat. No. 6,955,653.

(51) Int. Cl.
*A61D 5/00* (2006.01)
*A61F 2/02* (2006.01)
*B65D 81/00* (2006.01)
*A61B 10/00* (2006.01)
*A61B 18/04* (2006.01)
*A61B 18/18* (2006.01)

(52) U.S. Cl. ............... 600/582; 600/564; 600/565; 600/566; 600/567; 600/568; 606/34; 606/37; 606/38; 606/39; 606/40; 606/45

(58) Field of Classification Search ......... 600/562, 600/564–568; 606/34, 37–40, 45
See application file for complete search history.

(56) References Cited

U.S. PATENT DOCUMENTS

| | | | | |
|---|---|---|---|---|
| 5,683,384 | A * | 11/1997 | Gough et al. | 606/41 |
| 5,709,697 | A * | 1/1998 | Ratcliff et al. | 606/180 |
| 6,540,695 | B1 * | 4/2003 | Burbank et al. | 600/564 |
| 6,626,903 | B2 * | 9/2003 | McGuckin et al. | 606/45 |
| 6,936,014 | B2 * | 8/2005 | Vetter et al. | 600/564 |
| 6,958,044 | B2 * | 10/2005 | Burbank et al. | 600/564 |
| 2002/0072688 | A1 * | 6/2002 | Burbank et al. | 600/567 |
| 2003/0144605 | A1 * | 7/2003 | Burbank et al. | 600/564 |
| 2003/0195432 | A1 * | 10/2003 | Kortenbach et al. | 600/562 |

* cited by examiner

*Primary Examiner*—Max Hindenburg
*Assistant Examiner*—Jeffrey G Hoekstra
(74) *Attorney, Agent, or Firm*—Mueller Smith

(57) ABSTRACT

Electrosurgical tissue specimen recovery apparatus and system employing a multi-leaf capture component configured with pursing cables which are electrosurgically excited to define a cutting leading edge. To complete a capture, the cables are loaded in tension to purse and thus converge the tips of the capture component leafs together. The forward regions of the leafs are configured with a combination of a thin flat stainless steel region over which a polymeric cable guide is positioned. The polymeric cable guide and stainless steel leaf driving combination improves frictional aspects as well as the resulting aspect ratio of a recovered tissue specimen.

12 Claims, 9 Drawing Sheets

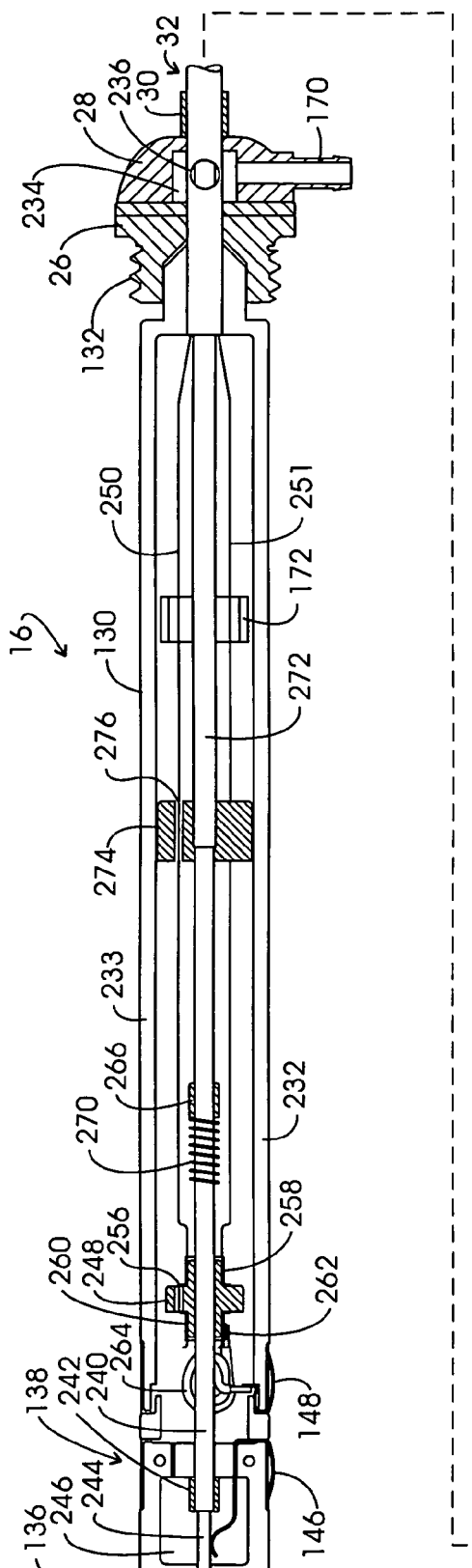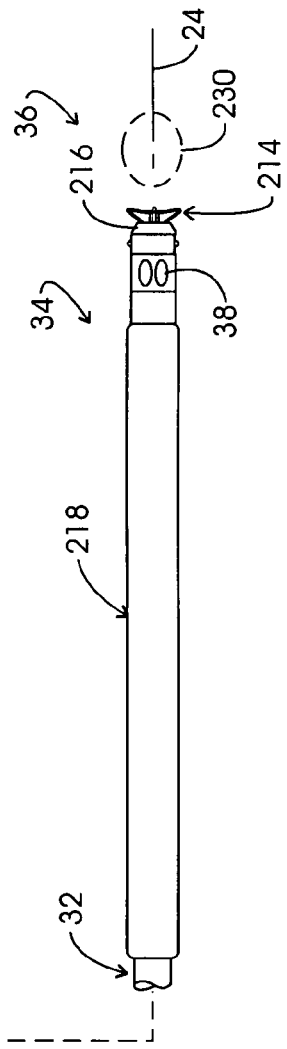
FIG. 4

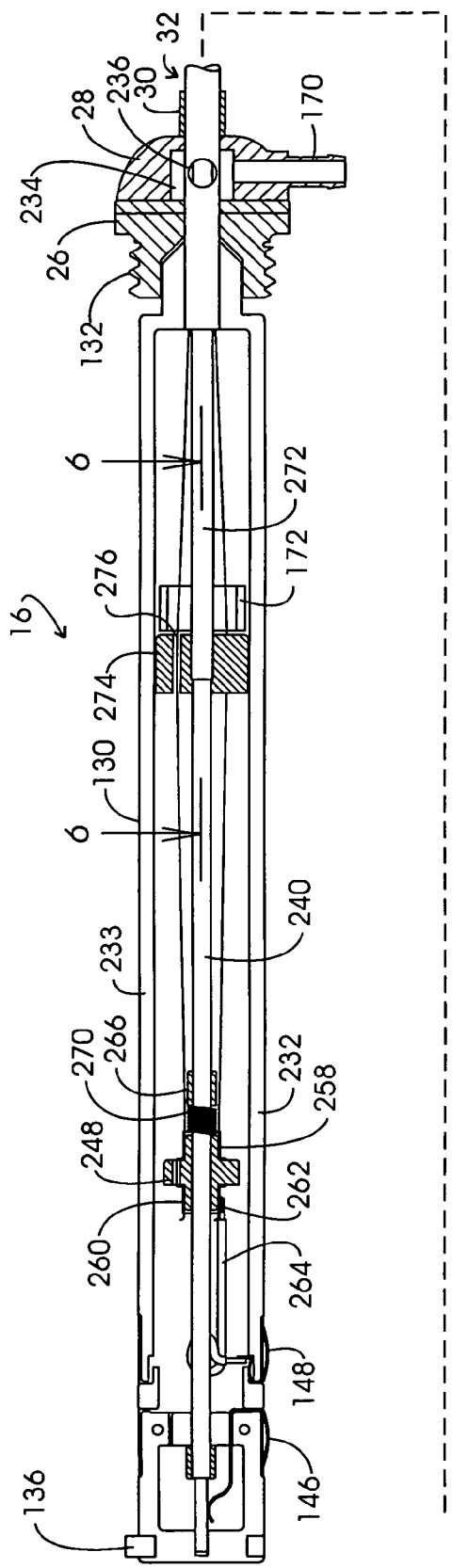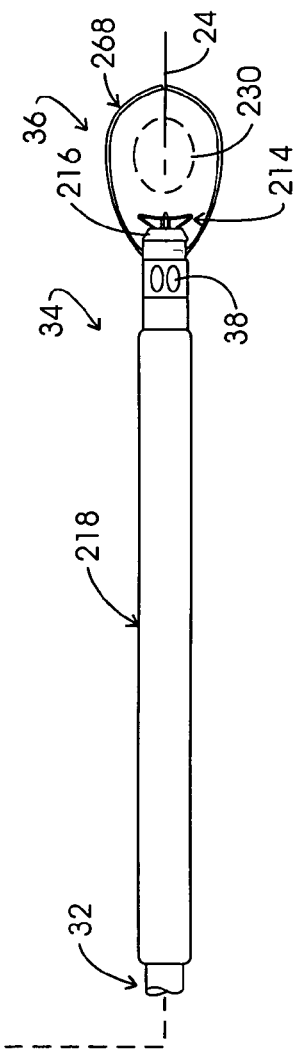
FIG. 5

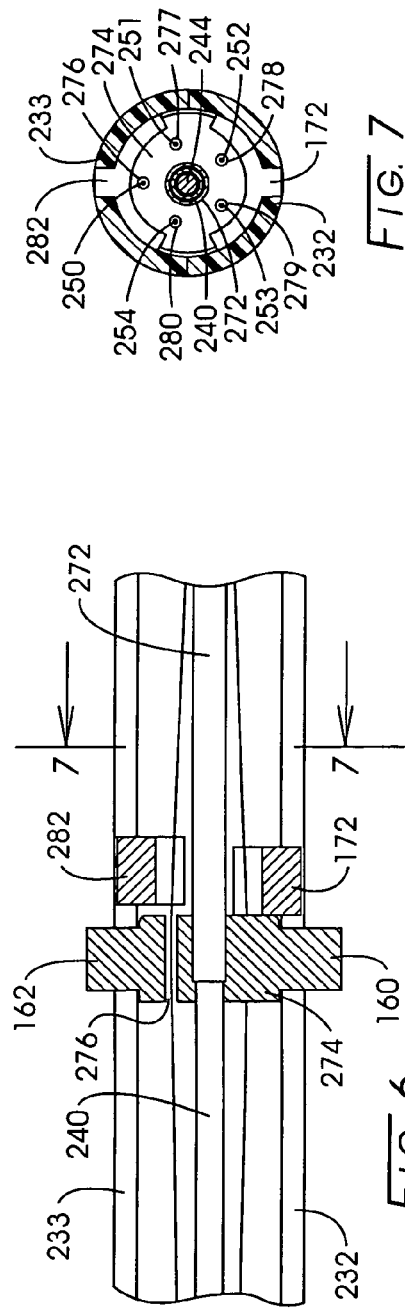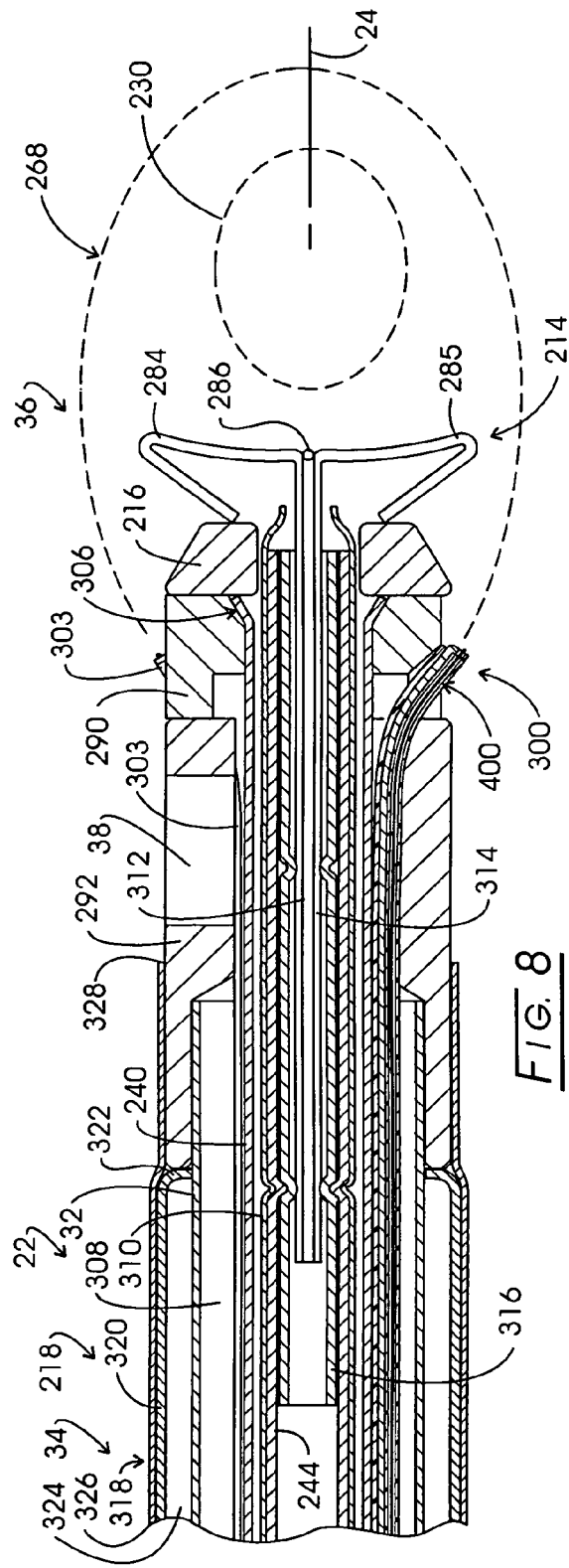

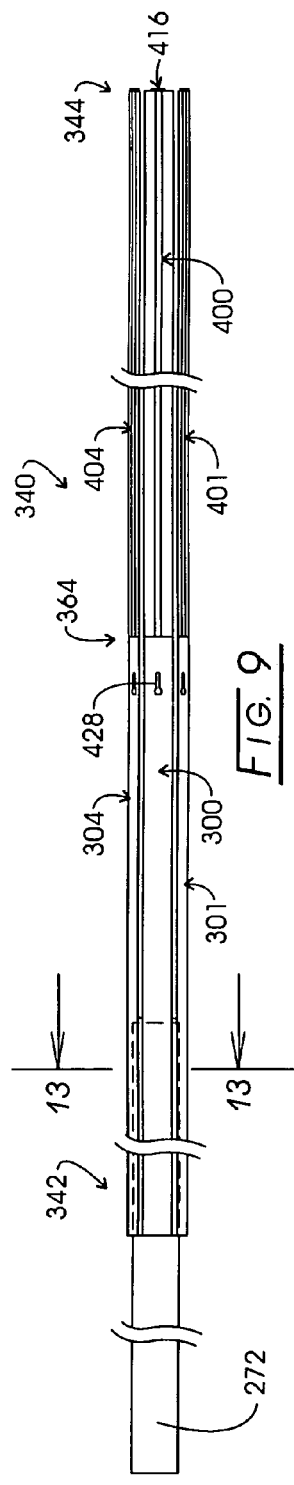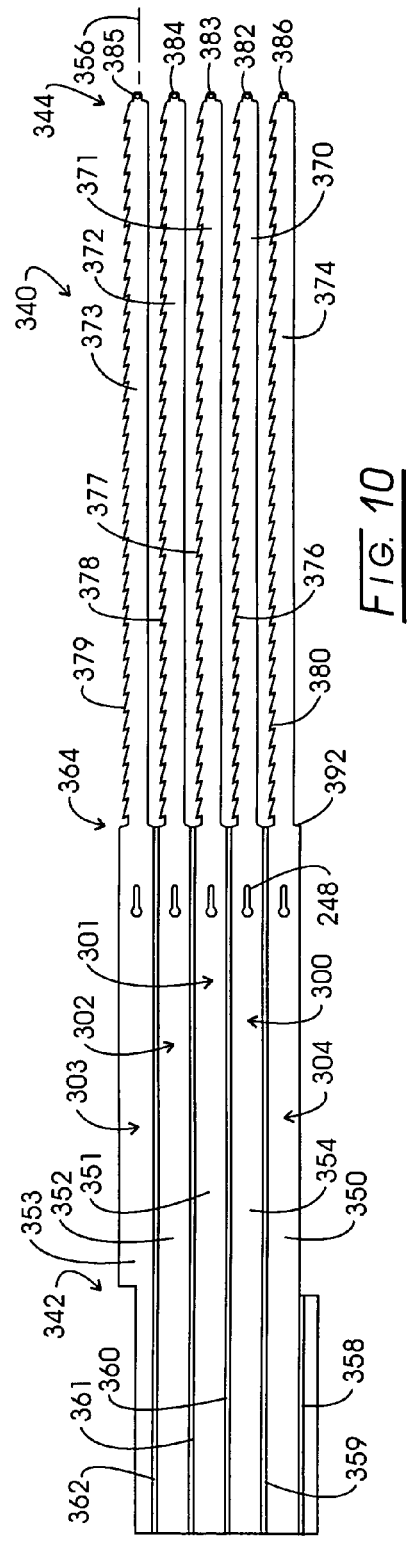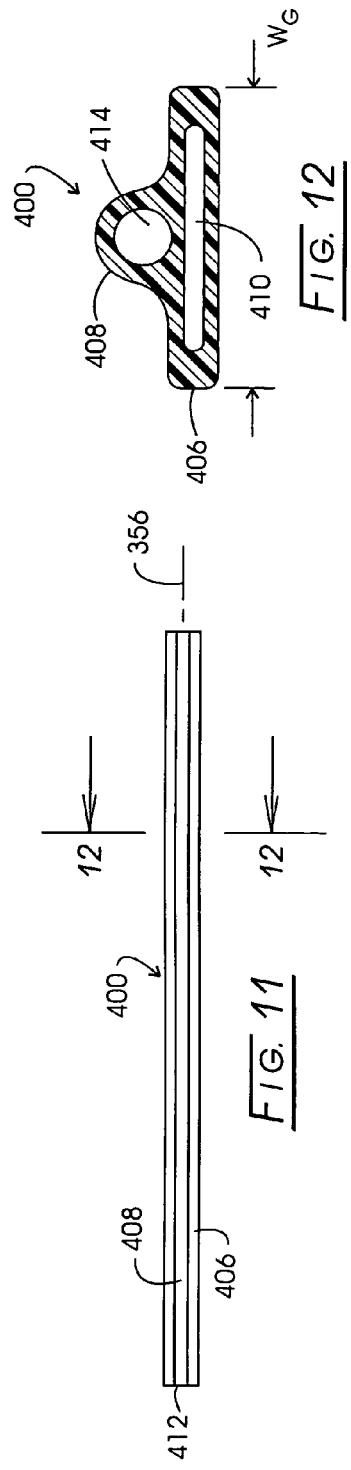

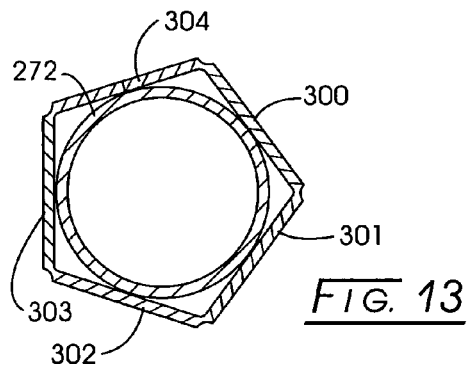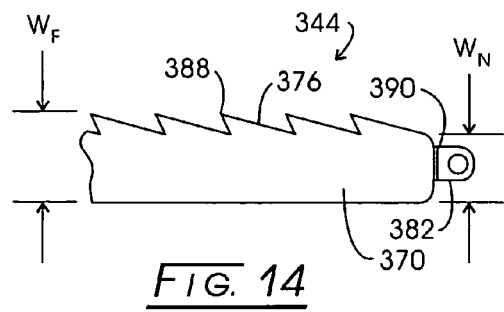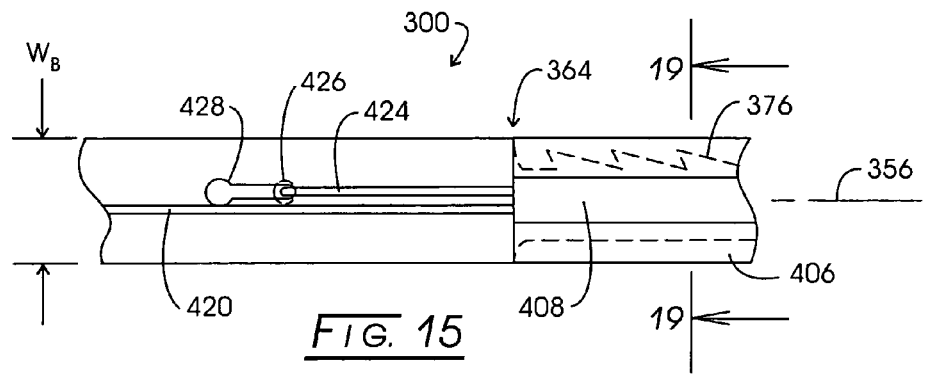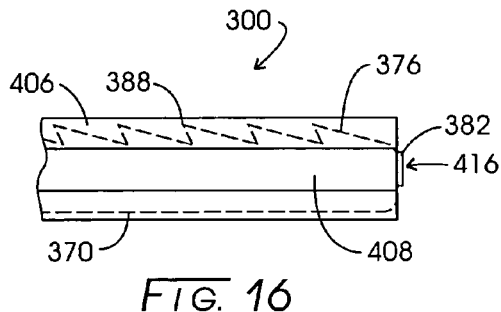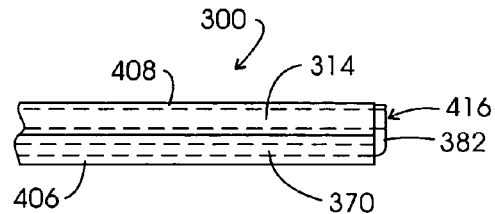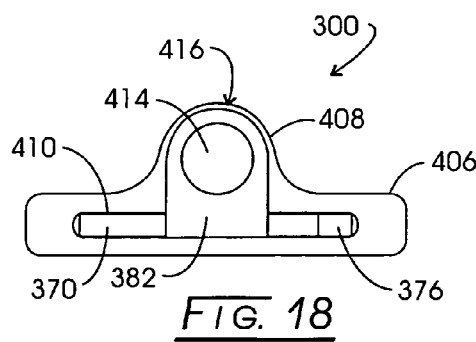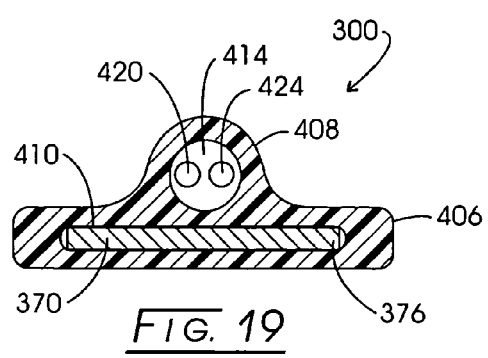

ELECTRICAL APPARATUS AND SYSTEM WITH IMPROVED TISSUE CAPTURE COMPONENT

CROSS-REFERENCE TO RELATED APPLICATIONS

This application is a continuation-in-part of prior application Ser. No. 10/630,336, filed Jul. 30, 2003 now U.S. Pat. No. 6,955,653.

STATEMENT REGARDING FEDERALLY SPONSORED RESEARCH

Not applicable.

BACKGROUND OF THE INVENTION

The detection of tumorous lesions in the breast has progressed from early observation and palpation procedures to a variety of somewhat sophisticated imaging systems. A consequence of these advances in tumor detection is the identification of suspect tumor at an early stage in its development. Generally, at such early stages the suspect tumor may be somewhat small. Rather than resort immediately to an open surgical resection upon such early detection, practitioners generally carry out a preliminary, minimally invasive biopsy procedure. Such preliminary biopsy approaches are of importance, inasmuch as statistically, only about 20% of these small tumors will be found to be malignant. Tumors determined to be benign have been left in situ with no excision. Over one million of these biopsies are performed in the United States each year, the procedure providing for the removal of part or all the suspect tissue for pathology examination and diagnosis. See generally:

(1) Rosen, Paul Peter, "Rosen's Breast Pathology", Lippincott-Raven Publishers, Philadelphia, 1997 pp 837-858.

One of the minimally invasive options is needle biopsy which may be either fine needle aspiration (FNA) or large core. Fine needle aspiration (FNA) is a procedure in which a fine needle, for example, of 21 to 23 gauge, having one of a number of tip configurations, such as the Chiba, Franzeen or Turner, is inserted into the breast and guided to the tumor site. A vacuum is created and the needle moved up and down along the tumor to assure that it collects targeted cellular material. Generally, three or more passes will be made to assure the collection of sufficient sample. Then, the needle and tissue sample are withdrawn from the breast for analysis.

The resulting specimen is subject to cytologic assay. In this regard, cell structure and related aspects are studied. This analysis has been used to improve or customize the selection of chemotherapeutic agents with respect to a particular patient.

While a fine needle aspiration biopsy has the advantage of being relatively simple, there are some drawbacks associated with its use. With fine needle aspiration, there remains a risk of false-negative results, which most often occur in cases involving extremely fibrotic tumor. In addition, after the procedure has been performed there may be insufficient specimen material for diagnosis. Finally, with fine needle aspiration alone the entire area of suspect tissue is not removed. Rather fragmented portions of tissue are withdrawn which do not allow a more advanced pathological investigation.

This limitation also is observed with respect to large core needle biopsies. For a large core needle biopsy, a 14 to 18 gauge needle is inserted in the breast having an inner trocar with a sample notch at the distal end and an outer cutting cannula. Similar to a fine needle aspiration, tissue is drawn through a needle by vacuum suction. These needles have been combined with biopsy guns to provide automated insertion that makes the procedure shorter and partially eliminates location mistakes caused by human error or lesion displacement. Once inserted, multiple contiguous tissue samples may be taken at a time.

Samples taken during large core needle biopsies may be anywhere from friable and fragmented to large pieces 20 to 30 mm long. These samples may provide some histological data, unlike fine needle aspiration samples. However, they still do not provide optimum pathological information. For further information concerning needle biopsy procedures see the following:

(2) Parker, Steve H, "Needle Selection and Sterotatic Large-Core Breast Biopsy", *Percutaneous Breast Biopsy* Eds. Parker, et al, Raven Press, New York, 1993 pp 7-14 and 61-79.

A device, which is somewhere between a needle biopsy and open surgery, is referred to as the Advanced Breast Biopsy Instrumentation (ABBI). With the ABBI procedure, the practitioner, guided by appropriate imaging, removes a core tissue sample of 5 mm to 20 mm in diameter. While the ABBI has the advantage of providing a large tissue sample similar to that obtained from an open surgical biopsy, the cylindrical tissue sample is taken from the subcutaneous tissue to an area beyond the suspect tumor. For tumors embedded more deeply within the breast, the amount of tissue removed is considerable. In addition, while less expensive than open surgical biopsy, the ABBI has proven expensive compared to other biopsy techniques, and it has been noted that the patient selection for ABBI is limited by the size and location of the tumor, as well as by the presence of very dense parenchyma around the tumor. See the following publications:

(3) Parker, Steve H., "The Advanced Breast Biopsy Instrumentation: Another Trojan Horse?", Am. J. Radiology 1998; 171:51-53.

(4) D'Angelo, Philip C., et al., "Sterotatic Excisional Breast Biopsies Utilizing The Advanced Breast Biopsy Instrumentation System", Am. J. Surg. 1997; 174: 297-302.

(5) Ferzli, George S., et al., "Advanced Breast Biopsy Instrumentation: A Critique", J. Am. Coll. Surg., 1997; 185: 145-151.

Another biopsy approach has been referred to as the mammotome and the Minimally Invasive Breast Biopsy (MIBB). These devices carry out a vacuum-assisted core biopsy wherein fragments of suspect tissue are removed with an 11-14 gauge needle. While being less invasive, the mammatome and MIBB yield only a fragmentary specimen for pathological study. These devices therefore are consistent with other breast biopsy devices in that the degree of invasiveness of the procedure necessarily is counterbalanced against the need of obtaining a tissue sample whose size and margins are commensurate with pathology requirements for diagnosis and treatment.

A minimally invasive approach to accessing breast lesions wherein the lesion is partially removed or removed in its entirety for diagnostic as well as therapeutic purposes has been described in U.S. Pat. No. 6,277,083 by Eggers, et al., entitled "Minimally Invasive Intact Recovery Of Tissue", issued Aug. 21, 2001. The instrument described includes a tubular delivery cannula of minimum outer diameter, the tip of which is positioned in confronting adjacency with a tissue volume to be removed. Following such positioning, the electrosurgically excited leading edge of a capture component is extended forwardly from the instrument forward region to enlarge while electrosurgically cutting and surrounding or encapsulating a tissue volume, severing it from adjacent tissue. Following such capture, the instrument and the encaptured tissue volume are removed through an incision of somewhat limited extent.

An improved design for this instrument, now marketed under the trade designation EN-BLOC® by Neothemia Corporation of Natick Mass., is described in U.S. Pat. No. 6,471,659 by Eggers, et al., entitled "Minimally Invasive Intact Recovery Of Tissue", issued Oct. 29, 2002. The EN-BLOC® instrumentation includes a tubular delivery cannula of minimum outer diameter, the tip of which is positioned in confronting adjacency with the target tissue volume to be removed. Such positioning is facilitated through the utilization of a forwardly disposed precursor electrosurgical electrode assembly. Located within the interior channel of this delivery cannula is a capture component configured with five relatively elongate and thin leafs which are mutually interconnected at their base to define a pentagonal cross-sectional configuration. Each of these leafs terminates forwardly at a tip region with a transversely bent forwardly extending eyelet structure. Slidably extending through each eyelet is an electrically conductive pursing cable of a pursing cable assembly. The tips additionally extend through a guidance assembly at the forward region of the delivery cannula. When the capture component is driven forwardly by the drive tube of a drive assembly, these leafs deploy outwardly and forwardly at an initial angle of attack of 35° to 45° while the pursing cables are "played out" and establish an electrosurgical cutting arc. Thus, cable movement defines a cutting profile that is extending outwardly at the noted 35° to 45° while moving forwardly to define an initial cutting profile extending circumferentially about the targeted tissue volume.

Drive imparted to the capture component from the drive tube is developed ultimately from an electric motor within the drive assembly. Each of the five pursing cables extends from the leading edge portion of the capture component through the delivery cannula to a cable terminator component which is pulled forwardly by the cable as the capture component forward portion moves from its initial position substantially within the interior channel of the delivery cannula toward an intermediate position wherein the electrosurgically excited leading edge leaf forward regions and associated pursing cables have achieved an effective maximum diametric extent. At this juncture, about one half of the targeted tissue volume will have been circumscribed by the capture component. At this position, the slidable cable terminator component will engage a cable stop component or collar. Forward movement of the attached cable assembly will be halted and a pursing action will ensue at the electrosurgical cutting leading edge wherein the tip regions of the cables are drawn inwardly with mutually inwardly directed angles of attack until the leaf tip portions converge at a capture position defining a capture basket configuration or tissue recovery cage substantially encapsulating the entire target tissue volume. As this position is reached, the tensioned cables permit no further movement and a stall condition is recognized at the drive motor to terminate electrosurgical excitation of the cable-defined leading edge of the capture component. Drive then is removed from the capture component by reversing the directional output of the electric motor.

An advantageous feature of this form of drive assembly for the capture component resides in an arrangement where the noted cable stop component which engages the cable terminator component may be adjusted longitudinally to, in turn, vary the extent of the effective maximum diameter developed by the leading edge of the capture component. For example, the device can be configured to recover tissue specimens of 10 mm, 15 mm, 20 mm or greater effective maximum diametric extent. With the system, capture is positive, minimally invasive and the procedure is of short duration, for instance, requiring about 7 seconds to recover a 10 mm maximum effective diameter tissue sample.

Studies undertaken with respect to the employment of this instrument in the recovery of tissue samples from very dense tissue including fibrous tissue have revealed that excessive drive motor current values may be encountered as the cables of its capture component are tensioned. Eggers, in application for U.S. patent Ser. No. 10/630,336 entitled "Electrosurgical Method and Apparatus With Dense Tissue Recovery Capability", filed Jul. 30, 2003, describes a modulated tensioning of the capture component to achieve effective recovery performance in very dense tissue.

The capture component of these instruments employs very minute elongate polyimide cable guide tubes which are affixed to centrally disposed chemically milled troughs at the center of the outwardly disposed surfaces of each leaf. Guide outlets of this tube then permit the cable to extend through metal eyelets integrally formed with the leafs themselves at their tip regions. The above-noted dense tissue studies led to improved designs of the eyelets as well as the selection of a braided stainless steel cable which exhibited higher tensile strengths under the high temperature conditions of an arc while remaining sufficiently flexible to carry out the deployment and pursing maneuvers called for with the instrument. Those studies are described by Eggers, et al., in application for U.S. patent Ser. No. 10/630,488, filed Jul. 30, 2003 and entitled "Minimally Invasive Instrumentation For Recovering Tissue".

Electrosurgical recovery of specimens with interstitially located or embedded cutting electrode presents a variety of unique conditions, one residing in the development of entrapped non-condensable gases and steam. These fluids, including excess unabsorbed anesthetic diluents, blood or other body secretions should be removed as they are encountered. Removal of gases and steam from the operative site as they are generated serves to (1) minimize the possibility of an embolism; (2) to minimize unwanted thermal damage to surrounding tissues; and (3) to minimize the exposure of the patient to the noxious smoke evolved during this procedure, the patient typically being awake, having been anesthetized only under local anesthetic. Liquid removal from the sample removal site serves to assure cutting arc maintenance at the interstitial locations involved. The evacuation subject is addressed by Eggers, et al., in application for U.S. patent Ser. No. 10/243,028, entitled "Electrosurgy With Infiltration Anesthesia", filed Sep. 13, 2002.

These fluid evacuation studies further extended to the potential of collateral thermal damage to both the tissue and skin of the patient occasioned by the evacuation implemented transmission of steam through the excision instrument itself. Electrosurgical cutting is achieved by disrupting or ablating tissue in immediate apposition to an excited cutting electrode, i.e., slightly spaced before it so as to permit the maintenance of a cutting arc. Tissues cells confronting this arc are vaporized. Some investigators have contemplated a model wherein cutting is achieved as the current heats the tissue up to boiling temperatures and the involved cells basically are exploded as a result of phase change. That phase change involves a generation of elevated temperature fluid including steam with attendant latent heat of vaporization.

Another parallel model has been described wherein, as intense electromagnetic field impinges on absorbing tissue, an acoustic wave is generated by the thermal elastic properties of the tissue. The origin of the pressure wave lies in the inability of the tissue to maintain thermodynamic equilibrium when rapidly heated. As with the above model, a consequence of the reaction is the generation of the elevated temperature fluid and attendant thermal phenomena. See generally:

(6) "Electrosurgery" by J. A. Pierce, John Wiley & Sons, New York, N.Y.

Studies directed to improve the EN-BLOC® system have been ongoing essentially since its inception. Manufacture of the capture component leafs and associated tubular cable guides has been successful but necessarily complex. Thus, investigators have looked to structures and fabrication techniques seeking to simplify this aspect of the device, preferably with a concomitant improvement in performance of the instrument.

BRIEF SUMMARY OF THE INVENTION

The present invention is directed to an electrosurgical apparatus and system for cutting about and retrieving a tissue volume with an improved capture component. This capture component generally is fashioned with a plurality of thin elongate leafs which extend from a base portion to tip regions having cable guide outlets. A pursing cable assembly configured with a plurality of electrosurgically energizable stainless steel multi-strand braided cables is supported by the multi-leaf structure in a manner wherein the cables are maneuvered through the guide outlets to establish a cutting leading edge which envelopes a target tissue volume as the moving leafs progressively assume the configuration of a tissue capturing cage. Each cable extends rearwardly within the associated instrument to connection with a slidable terminator component. By blocking the movement of the terminator component as the cable assembly defines a maximum diametric extent, a pursing action ensues as the tips of the leafs converge toward the instrument axis. With the present invention, a forwardly disposed stainless steel guide support region of each leaf is formed with a diminished widthwise extent and is enclosed within an extruded polymeric cable guide. This not only provides an improved leaf cable guide function but permits enhanced flexure at the tip region of each leaf. That enhanced flexure promotes a steeper angle of attack during the pursing activity to, in turn, improve the cutting profile of the advancing and pursing cutting cable leading edge.

The improved leaf forward region flexibility is accommodated for with respect to determining the completion of a capture maneuver by the provision of a capture stop within the instrument itself which blocks leaf drive and evokes a motor stall condition which is utilized as a signal to terminate the capture activity. In addition to providing a very positive termination of capture signal, utilization of the capture stop avoids any unwanted curling or flexure at the leaf tip regions following their reaching a full pursing orientation.

The cable guides are formed as polytetrafluoroethylene (Teflon) extrusions and thus, exhibit a surface friction characteristic which is improved over the corresponding surface characteristic of earlier utilized stainless steel capture component leafs. Utilization of such extruded cable guides into which the forward stainless steel leaf components are inserted substantially lessens the complexity of fabrication of the capture component with an attendant improvement in manufacturing costs.

Other objects of the invention will, in part, be obvious and will, in part, appear hereinafter. The invention, accordingly, comprises the system and apparatus possessing the construction, combination of elements and arrangement of parts which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIG. 4 is a partial sectional view of the disposable component of the instrument shown in FIG. 2, schematically showing the orientation of its components prior to the deployment of a capture component;

FIG. 5 is a partial sectional view of the disposable component of the instrument shown in FIG. 2 illustrating the orientation of components at a point in a procedure wherein capture is very close to completion;

FIG. 6 is a partial section view of a drive component, capture stop and safety stop in their orientation at the completion of a capture procedure;

FIG. 7 is a sectional view taken through the plane 7-7 shown in FIG. 6;

FIG. 8 is a partial sectional view of the forward region of the disposable component of the instrument of FIG. 2;

FIG. 9 is a side view of a capture component according to the invention at a stage in its fabrication prior to the installation of a pursing cable assembly;

FIG. 10 is a top view of the base and guide support region of a leaf structure of the capture component of FIG. 9 illustrating its shape following chemical milling;

FIG. 11 is a top view of a guide component employed with a capture component of the invention;

FIG. 12 is a sectional view taken through the plane 12-12 shown in FIG. 11;

FIG. 13 is a sectional view taken through the plane 13-13 shown in FIG. 9;

FIG. 14 is an enlarged top view of a capture component leaf guide support region shown in FIG. 10;

FIG. 15 is a top view of a completed capture component leaf shown in FIG. 9;

FIG. 16 is a partial top view of a cable guide and associated guide support region showing the orientation of a protective aperture at an assembly stage prior to the installation of cable components;

FIG. 17 is a side view of the capture component leaf forward Up region shown in FIG. 16;

FIG. 18 is a front view of the leaf tip region shown in FIG. 18;

FIG. 19 is a sectional view taken through the plane 19-19 shown in FIG. 15;

DETAILED DESCRIPTION OF THE INVENTION

In the discourse to follow, the above-discussed EN-BLOC® system is described in order to facilitate an understanding of the general design and operation of the capture component of the instrument and system at hand. As the description unfolds, the improvements to the capture component and its associated drive are detailed.

Figure 1:
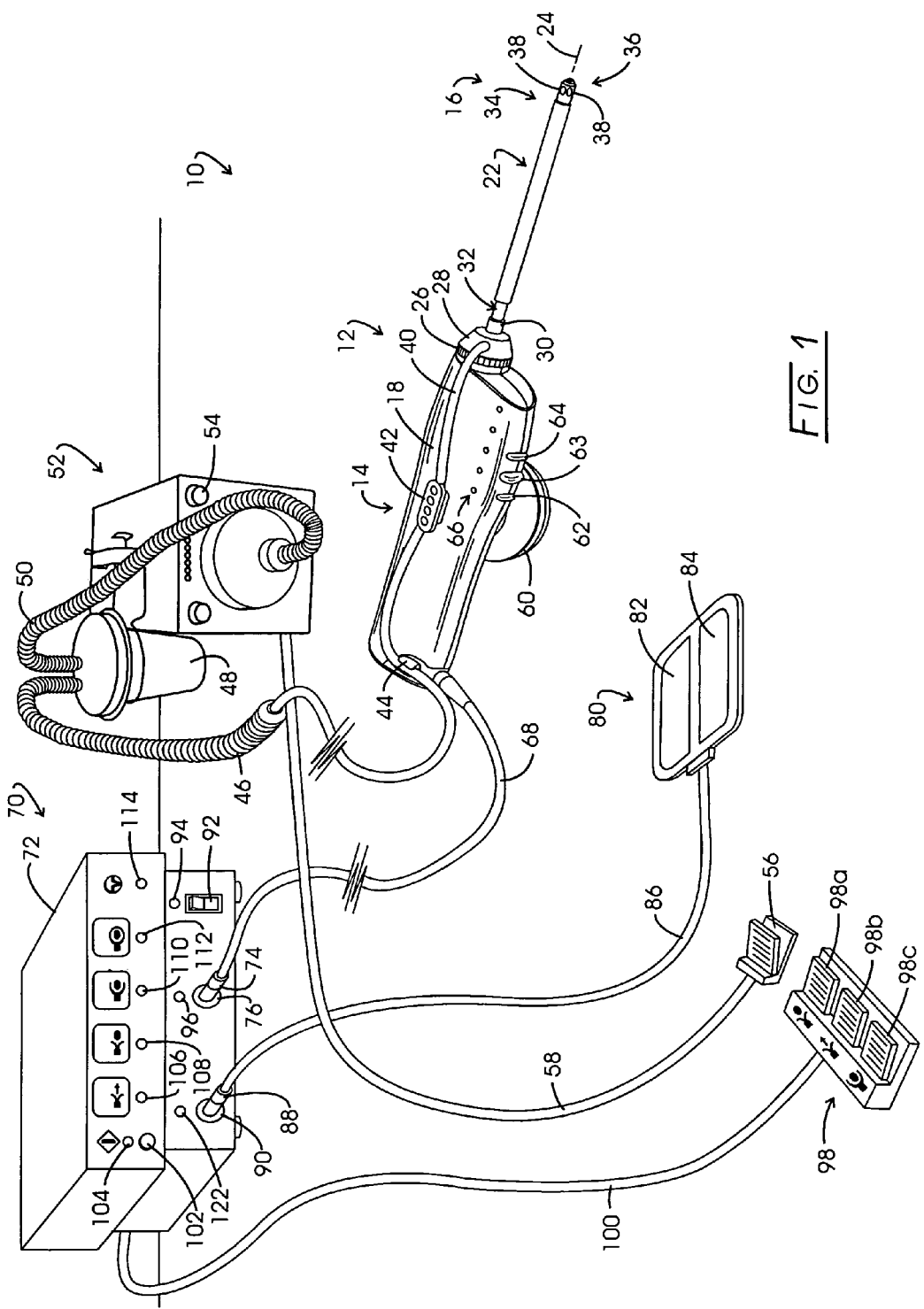
FIG. 1 is a perspective view of an electrosurgical system according to the invention.

Referring to FIG. 1, the system for isolating and retrieving a target tissue volume or biopsy sample is illustrated in general at 10. System 10 comprises a tissue retrieval instrument represented generally at 12 which includes a reusable component represented generally at 14, sometimes referred to as a "handle". Instrument 12 additionally includes a disposable component represented generally at 16, the rearward portion of which is removably mounted within the polymeric housing 18 of reusable component 14. The disposable component 16 is sometimes referred to as a "probe".

Disposable component 16 includes an elongate cannula or support assembly represented generally at 22 which extends along an instrument axis 24. The proximal end of cannula or support assembly 22 extends through a rotatable connector 26. Connector 26, in turn, is threadably engaged within housing 18. Support assembly 22 additionally extends through a rotatable suction manifold 28 which is a component of an evacuation system. Manifold 28 is retained in position on support assembly 22 by a ferrule or collar 30 which is mounted over the outward surface of a support tube, a portion of which is represented in general at 32. Most of the outward surface of the support assembly 22 will be seen to be covered with an electrically insulated thin polyolefin shrink-wrap or tube. The forward region of the support assembly 22, as represented generally at 34 extends to a distal end or tip represented generally at 36. Suction or vacuum manifold 28 is in vacuum conveying and fluid receiving relationship through support assembly 22 with four intake ports located at forward region 34, two of which are shown at 38. The evacuated fluids will be at an elevated temperature due to the electrosurgical nature of the instrument 12 and generally will include non-condensable gases such as smoke, in addition to fluids such as blood and accumulations of local anesthetic solution. Vacuum is conveyed to and the elevated temperature fluid is received from suction manifold 28 via a flexible transparent polymeric tube 40. Tube 40 extends from an evacuation outlet (not shown) at manifold 28 to a press-fit connection with connectors 42 and 44, whereupon it is coupled with a flexible tube or hose 46 of larger diametric extent. Hose 46 extends to a fluid trap and filter assemblage 48 which is in vacuum communication via flexible hose 50 with the suction input of a suction pump assembly represented generally at 52. Vacuum or suction pump assembly 52 may be of a type marketed under the trade designation: "VersaVac 2" by Stackhouse, Inc. of Palm Springs, Calif. Pump assembly 52 may be actuated into operation from a switch arrangement represented generally at 54 or through the utilization of a footswitch 56 coupled to the pump assembly 52 via a cable 58.

Connectors as at 42 are positioned on each side of the housing 18 and function additionally where not employed to retain tubes as at 40 to support a stabilizer hand grip, for example, the annulus-shaped grip represented at 60. Connectors as at 42 also may be employed to support the instrument 12 for sterotatic manipulation. Positioned at the forward portion of the housing 18 are three button switches 62-64 which function respectively as an arm/disarm switch; an energize/position switch; and a start tissue capture switch. Immediately above the switches 62-64 on each side of housing 18 are linear arrays of light emitting diode (LED) based indicator or cueing lights, one such array being represented generally at 66. The visual cues provided by the indicators at array 66, from the forward region of housing 18 toward the rear region thereof, provide a start/reset cue as a green light; a tissue capture complete cue provided as a green light; a start tissue capture cue (above switch 64) provided as a yellow light; an energize/position cue (above switch 63) provided as a yellow light; and an arm/disarm cue (above switch 62) provided as a green light.

Energization and electrical control is provided to the instrument 12 via a multi-lead cable 68 which connects with a combined control assembly and electrosurgical generator represented generally at 70 and incorporated within a console 72. The control assembly components within console 72 perform in conjunction with counterparts incorporated within instrument 12 and principally within reusable component 14. Assembly 70 may be provided as a model "3000 RF Controller" marketed by Neothermia Corporation (supra). Connection of the cable 68 with the console 72 is shown at a multi-lead connector 74 which is coupled to a console connector 76. The electrosurgically active electrode assembly of the instrument 12 performs in monopolar fashion. Thus, a conventional, relatively large dispersive return electrode assembly as shown in general at 80, is positioned against the skin surface of the patient. Assembly 80 is configured as having two electrode components 82 and 84 which are connected via cable 86 and connector 88 to console connector 90. Alternately, a return electrode may be positioned at the surface of cannula or support assembly 22 near its distal end in place of the illustrated use of dispersive return 80.

Power is supplied to the circuitry at console 72 upon actuation of an on/off switch 92. When switch 92 is in an "on" orientation, a green visual indicator LED 94 located above the switch is energized. Proper connection of the cable 68 and connector 74 with console connector 76 is indicated by an illuminated green LED 96 positioned above connector 76. This connection test is carried out by directing current to a coding resistor within housing 18. A three-pedal footswitch represented generally at 98 is coupled via a cable 100 to the rear panel of console 72. The three pedals, 98a-98c of switch 98 emulate and provide alternative switching with respect to button switch at 62-64.

Visual cueing corresponding with that at housing 18 LED arrays as at 66 also is provided at the console 72. In this regard, a start/reset switch 102 is operationally associated with an LED indicator 104 which illuminates in a green color upon actuation of that switch. An energize/position mode visual cue LED representing an energization of a precursor electrode assembly at tip 36 is shown at 106. This LED provides a yellow output during the electrosurgical advancement of cannula or support assembly tip 36 into confronting adjacency with a targeted tissue volume. Next, a green, arm/capture mode visual cue is provided by LED 108 to represent an arming of the tissue capture feature of instrument 12. Once an arm/disarm switch as at 62 or 98a is depressed, the energize/position switches as at 63 or 98b are no longer activatable. However, the practitioner may return to the positioning mode by again depressing an arm/disarm switch. To enter the capture mode, the practitioner depresses footswitch 98c or capture switch 64. A yellow capture mode visual cue is provided by an LED 110 to represent the start of and carrying out of a tissue capture or retrieval procedure and upon completion of such capture, a green capture complete visual cue is provided by green LED 112. A pause mode condition is represented by the energization of green LED 114. In general, the pause mode is entered during a procedure by releasing capture switch 64 or footswitch 98c. When in a pause mode, the active capture electrodes of the instrument 12 are not energized and deployment of its capture component is halted. However, that evacuation function carried out by the suction pump assembly 52 continues to perform. To reenter the capture mode, the practitioner again depresses footswitch 98c or capture switch 64. Upon re-actuation of the chosen switch, the capture mode continues, in effect, from the orientation where it left off. This pause mode of operation of the system may be employed by the practitioner during a capture mode of operation to permit, for example, the evacuation of fluids encountered by arc-based cutting components. Such fluids may, for example, be accumulations of local anesthetic solution, blood or the like.

An assurance that the vacuum system is operating, at least to the extent that the vacuum pump assembly 52 is active, can be accomplished with a vacuum actuated switch (not shown) attached with the conduiting extending between the pump assembly 52 and the instrument 12. For example, unless such a switch is actuated, the commencement of a procedure can be logically blocked by the control assembly 70. In addition to the removal of smoke and such fluids as are discussed above, the evacuation system including pump assembly 52, conduiting defining a transfer channel extending to the intake ports 38, functions to remove steam which is generated by the encounter of an electrosurgical cutting arc with fluid of tissue cells. This removal of steam serves, inter alia, to protect healthy tissue surrounding the region of cutting from thermal trauma.

At the time the connector 88 of return electrode 80 is coupled to console connector 90 and switch 92 is in a power-on condition, a patient circuit safety monitor (PCSM) carries out a self-test. On subsequent actuation of the start/reset switch 102, a fault test with respect to the two electrode components 82 and 84 is performed. In the event the latter test fails, then both visual and aural pulsating warning cues are activated, the visual cue being provided as a red LED 122 located adjacent connector 90.

Figure 2:
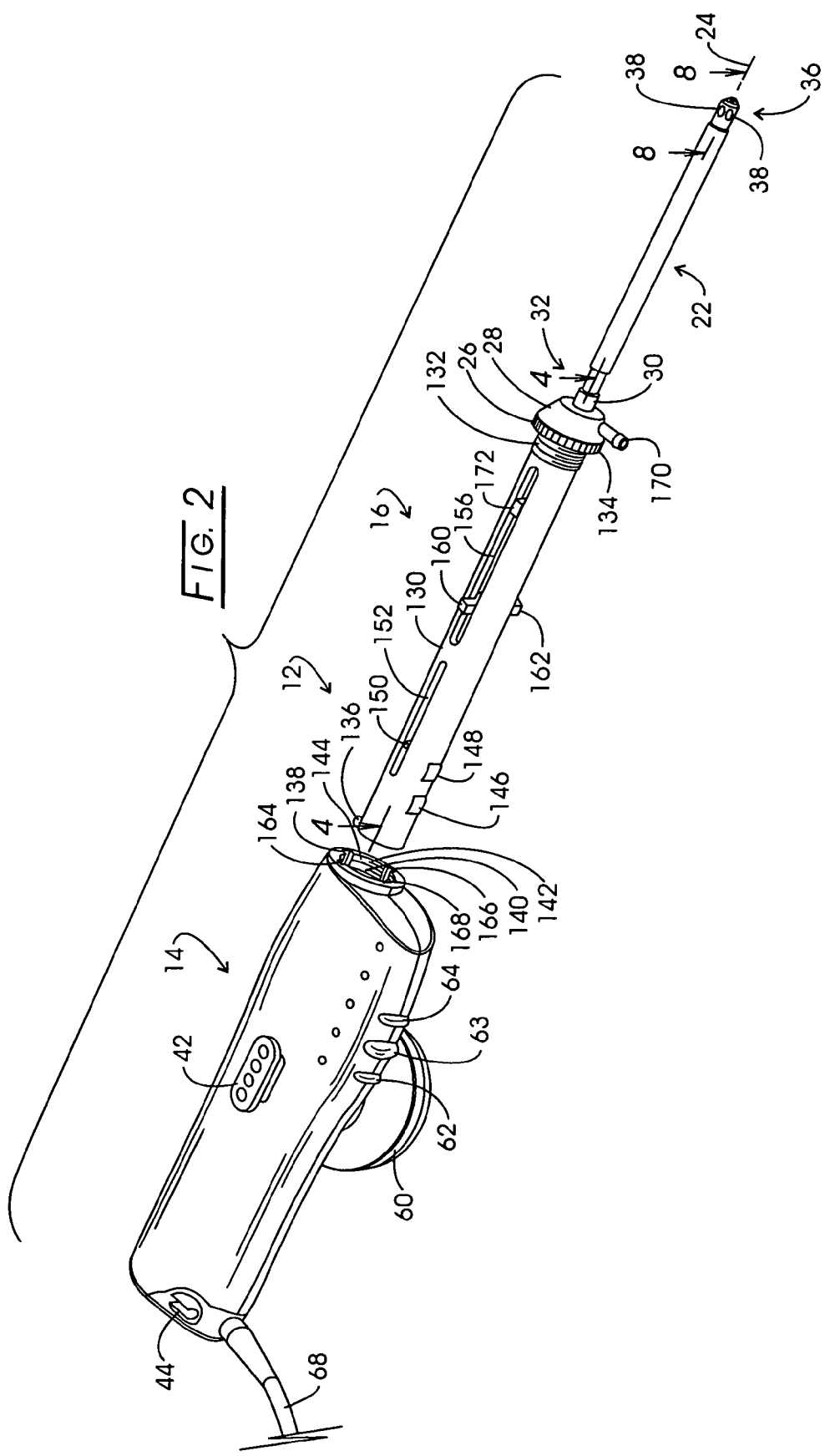
FIG. 2 is an exploded view of an electrosurgical instrument shown in FIG. 1.

Referring to FIG. 2, the disposable component 16 of instrument 12 is revealed in an orientation prior to its insertion within the housing 18 of reusable component 14. In the figure, cannula or support assembly 22 is seen extending forwardly from a cylindrically-shaped support housing 130. The forward region of support housing 130 supports the rotatable connector 26. In this regard, it may be observed that the connector 26 is configured with external threads 132 which are affixed for rotation with a grasping surface 134 formed in scalloped fashion to facilitate its hand rotation. At the rearward end of support housing 130 there is located an upstanding indexing pin 136 which, during installation of the disposable component 16, is slidably received within an upwardly disposed elongate slot 138 extending internally along an elongate receiving cavity 140. The forward end of receiving cavity 140 of housing 18 is formed by an alignment bushing 142 having internal threads 144. Internal threads 144 of alignment bushing 142 within cavity 140 threadably engage the external threads 132 of connector 26 when the disposable component 16 is mounted with the reusable component 14.

Positioned opposite indexing pin 136 on support housing 130 are two, spaced apart electrical contacts 146 and 148 which are oriented to make wiping contact with corresponding electrical terminals disposed within housing 18 upon insertion of support housing 130 within the receiving cavity 140. Contacts 146 and 148 selectively receive electrosurgical cutting current which is applied respectively to a precursor electrode assembly at tip 36 and to the electrosurgical cutting and pursing cables associated with a capture component initially retained within support assembly 22. Those pursing cables extend from the capture component within support component 22 to a cable terminator component having guidance tabs or ears, one of which is revealed at 150 slidably mounted within an elongate stabilizer slot 152 arranged in parallel with axis 24. A corresponding guidance tab and slot combination is found on the opposite side of support housing 130. Located forwardly of the slots as at 152 are two elongate drive slots, one of which is shown at 156 similarly arranged in parallel with axis 24. The outwardly extending ears or guide tabs of a drive assembly drive member extend from these slots and are seen at 160 and 162. These ears or tabs 160 and 162 support rearwardly disposed driven surfaces which are used to impart forward movement to the drive assembly components. This forward movement functions to deploy the noted capture component from cannula component 22. When the support housing 130 is installed within the receiving cavity 140 of housing 18, these tabs 160 and 162 pass through oppositely disposed notches shown respectively at 164 and 166 provided at the forward portion of housing 18 as part of alignment bushing 142. Similarly, a notch 168 is located forwardly within housing 18 to permit passage of the electrical terminals 146 and 148. Alignment bushing 142 is configured to form the forward portion of elongate slot 138 and notch 168.

The procedure for installing the disposable component 16 within reusable component 14 involves the sliding of support housing 130 within the receiving cavity 140 and the rotating of grasping surface 134 of connector 26 to provide for the engagement of threads 132 with threads 144. Upon completing the assembly, the flexible transparent tube 40 (FIG. 1) of the evacuation assembly may be attached to an evacuation outlet 170 depending outwardly and in fluid and suction or vacuum communication with suction manifold 28. Finally, a tab as at 172 is seen extending within a forward portion of the drive slot 156. This tab is a portion of a capture stop which will be seen to be an operational aspect associated with the capture component revisions of the invention. The capture stop incorporating tab 172 will be seen to be associated additionally with a safety stop (FIGS. 6 and 7) disposed oppositely therefrom. This capture stop incorporating tab 172 is located in correspondence with a capture complete orientation of the capture component functioning to evoke a motor stall condition and attendant shutdown of electrosurgical excitation activity.

Figure 3:
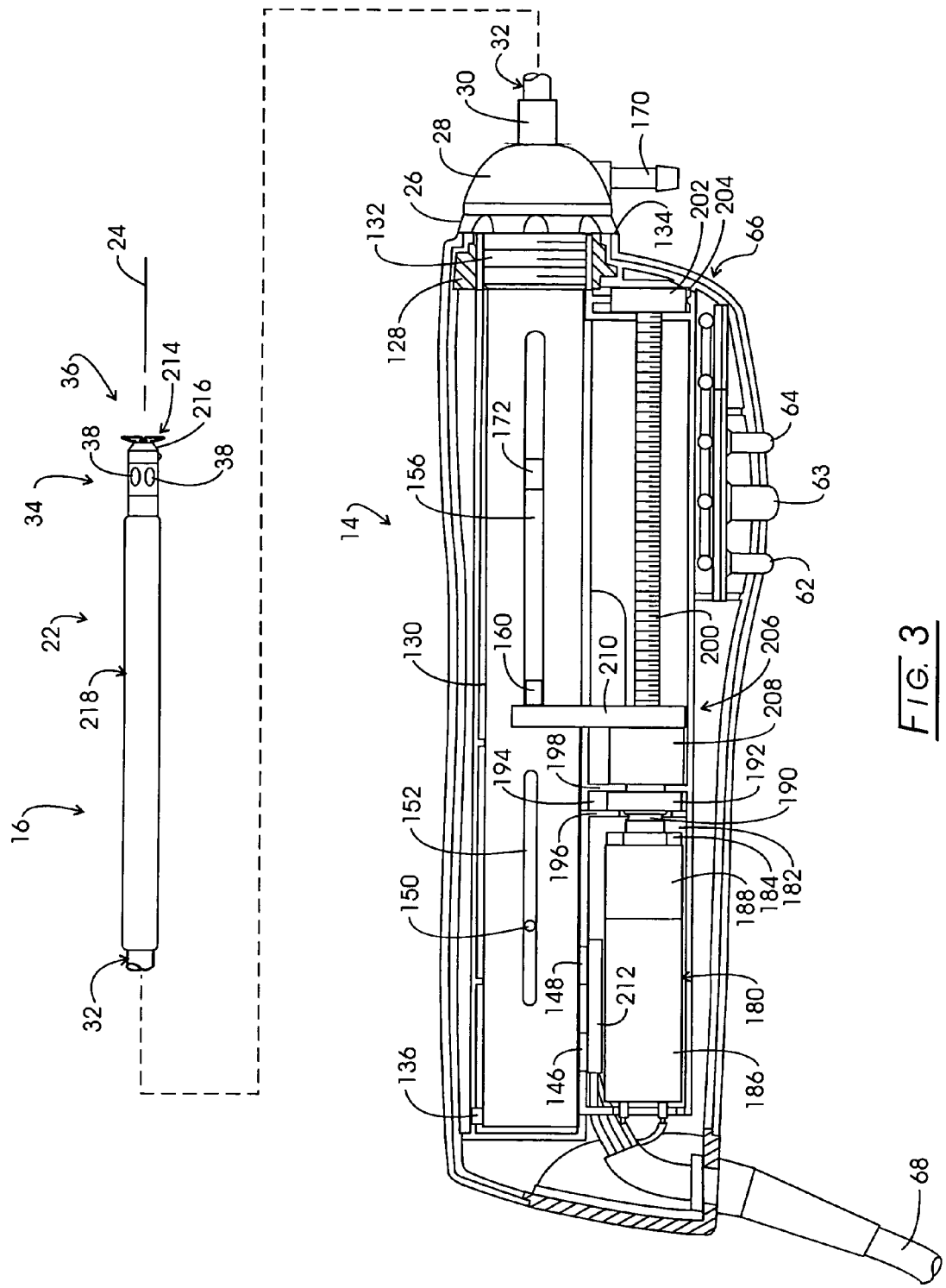
FIG. 3 is a partial sectional view of the instrument shown in FIG. 2 with portions broken away.

Referring to FIG. 3, a sectional view is presented illustrating the operative association of motor drive features of the reusable component 14 with the support housing 130 of disposable component 16. In the figure, a motor assembly represented generally at 180 is seen to be located within a motor mount chamber 182. In that chamber 182 the motor assembly 180 is permitted some self-aligning movement but is restrained from rotational movement by a torque stop component 184. Motor assembly 180 incorporates a motor component 186 which is coupled in driving relationship with a planetary gear assembly 188. The drive output of the planetary gear assembly 188 is connected in driving relationship with a stainless steel flexible bellows-shaped coupler 190 which extends through a fluid seal 192 located within a seal chamber 194 defined by oppositely disposed and spaced apart bulkheads 196 and 198. Seal 192 does not constrain the coupler 190 and permits the noted self-alignment of motor assembly 180 with respect to its coupling to a rearward end of an elongate threaded translation component 200. The forward end of translation component 200 extends into engagement with a thrust bearing 202. Bearing 202 provides support against all of the driving forces imposed from the motor assembly 180 and is mounted and secured within a thrust bearing chamber 204. Translation component 200 is threadably engaged with a transfer assembly represented generally at 206 which comprises a ball screw or nut component 208 and a generally Y-shaped yoke 210 which is configured to extend to a position aligned for driving but freely abutting engagement with tabs or ears 160 and 162 (FIG. 2). During a capture procedure, the translation component 200 is drivably rotated in an appropriate direction to move the transfer assembly 206 forwardly. That movement, in turn, urges a drive component forwardly until capture component pursing activity is completed and the motor component 186 enters a stall condition. At that juncture, the control system halts electrosurgical cutting current and reverses the directional drive sense of motor 186 to cause the transfer assembly 206 to return to a "home" position generally illustrated in the instant figure. The figure additionally reveals that the two electrical contacts 146 and 148 located upon support housing 130 will be in contact with corresponding contacts (not shown) supported by a polymeric ledge 212.

FIG. 3 also reveals some details of the tip 36 of the support assembly 22. The tip incorporates four precursor electrode components arranged in a cross-shape or symmetrically about axis 24 as is represented in general at 214. These precursor electrodes are located just forwardly of a truncated cone-shaped ceramic (alumina) protective tip component 216. Tip component 216 functions to provide an arc-resistant or arc isolating tip portion preventing its breakdown.

A more detailed description of the system 10 including the control assembly 70 and the drive system within housing 18 is provided in the above-referenced U.S. Pat. No. 6,471,659 which is incorporated herein by reference.

The forward drive movement of transfer assembly 206 by motor assembly 180 and translation component 200 serves to impart forward drive to a drive member within cylindrical support housing 130 which, in turn, drives forwardly a drive tube or component functioning to deploy a capture component, the leading edge of which is provided as an electrosurgically cutting pursing cable assembly having an initially expanding and then contracting effective diametric extent. When then deployed, the capture component circumferentially cuts around the target tissue volume and thus isolates and encapsulates a resultant tissue sample for removal. Support assembly 22 also is shown having a slightly enlarged central region represented generally at 218. Region 218 will be seen to incorporate a thermal shield functioning to avoid trauma to adjacent tissue during the evacuation of steam as well as other components through the intake ports 38.

As a prelude to describing the improved capture component leaf structure of the invention, the discourse now turns to the mechanism which serves to drive those capture components leafs from their initial orientation to a pursed down capture complete one wherein they will have cut about and enclosed the target tissue sample.

FIGS. 4 and 5 provide partial sectional exploded views of the disposable component 16 as it is positioned in confronting relationship with a target tissue sought to be retrieved as represented symbolically at 230. Looking to FIG. 4, an initial stage in the procedure employing the instrument 12 is represented wherein tip 36 is in confronting relationship with the symbolic target tissue 300. In this orientation, the capture component located within cannula or support tube 32 will be in an initial position. Support housing 130 is formed of two identical moldings, 232 and 233. These paired moldings are retained together adhesively as well as by connector 26 which, additionally, supports cannula or support tube 32. Tube 32 extends through an evacuation chamber 234 formed within manifold 28. Vacuum communication with the chamber 234 is provided by a port or opening 236 in component 32.

Extending from adhesive attachment at a rearward bulkhead represented generally at 238 defined by the paired molding components of housing 130 is the inward portion of a support tube 240. Tube 240 will be seen to extend from its attachment with bulkhead 238 to the region of tip 36. Tube 240 is anchored at the rearward side of bulkhead 238 by a plastic collar 242. Extending through the interior of the support tube 240 is a precursor electrode tube 244, the rear tip of which extends along axis 24 into engagement with the paired molding components 232 and 233 at a cavity 246. That portion of the precursor electrode tube 244 which extends rearwardly from support tube 240 is configured with an electrically conductive surface which receives electrical precursor electrode current through resiliently biased terminal component 146. The remainder of the precursor electrode tube 244, as it extends within support tube 240 is covered with an electrically insulative shrink-wrap. The capture component is configured with five, 19-strand braided stainless steel cables which extend therefrom within support component 32 to a polymeric cable terminator component 248 which is slidably mounted over support tube 240 and moveable thereon in parallel with instrument axis 24. Two of the noted braided pursing cables are stylistically represented in the drawing at 250 and 251. However, all five of these cables extend to and are connected with the cable terminator component 248. Component 248 is formed with five longitudinally disposed and radially spaced channels into each of which one of the five cables extend. In FIG. 4, cable 250 is seen extending through a channel 256. All five cables are retained or fixed to the terminator component 248 by two stainless steel collars. In this regard, a forward stainless steel collar or ferrule is shown at 258, while a rearward one is shown at 260. Collar 260 additionally functions to apply electrosurgical cutting power or current simultaneously to all five of the pursing cables and, accordingly, it initially is nickel plated and then gold plated such that electrosurgical cutting current may be applied to it through a solder union 262. Union 262 connects the collar 260 with a multi-strand and highly flexible insulated copper cable 264. Cable 264, in turn, is soldered or welded to the forward electrical terminal assembly 148. Terminator component 248 is stabilized for slidable movement by two outwardly extending guide tabs or ears, one of which has been described at 150 in FIGS. 2 and 3. With this arrangement, as the five cables are electrically excited with electrosurgical cutting current, they are drawn in minor tension forwardly to, in turn, pull the terminator component 248 in slidable fashion axially forwardly over the support tube 240. This minor amount of tension is represented symbolically at cables 250 and 251 by a geometric angularity. This sliding movement under the drive of cable tension continues until the cable terminator 248 encounters a cable stop 266 which is fixed to support tube 240 at a location which is selected to establish the maximum effective diametric extent of opening and overall length of the containment structure or cage generated by the capture component. Such a cage is symbolically represented in general profile at 268 in FIG. 5. Note that the cage-like profile 268 surmounts the target tissue 230. The location of the cable stop 266 is the only adjustment required for developing a variation in the effective maximum diametric extent and length dimensioning of the capture component. In this regard, that effective diametric extent may range from about 10 mm to about 40 mm.

In general, cable stop collar 266 is located such that the sliding movement of terminator component 248 is blocked when the capture component achieves the intermediate position generally representing about one half of its longitudinal deployment and a maximum effective diametric extent. The capturing performance of instrument 12 may be importantly improved such that its use may extend to the recovery of very dense tissue by deriving a pursing stress on the cables which progressively increases toward a higher value generally established by full blockage at cable stop 266. This progressive cable loading occurs as terminator component 248 approaches stop 266 and is implemented by the positioning of a resilient component present as a compression spring 270 located in abutment with cable stop 266. Note that the spring 270 extends rearwardly along support member 240 from its abutting engagement with stop 266. With the arrangement, helical compression spring 270 functions to modulate the extent of tension applied to the cable such that the tips of the capture component leafs are vectored inwardly toward axis 24 in a more gradual fashion as pursing activity commences. For performance in conjunction with capture configurations of from about 10 mm to about 15 mm maximum effective diametric extent, spring 270 will have a length of about 0.25 inch, a solid height of about 0.1 inch and a spring rate of about 7 to 10 pounds per inch.

Drive imparted to the capture component to cause its leafs to deploy is developed from a drive tube or component 272 which extends within support or cannula component 272 from the base of the capture to component connection with a drive member 274. As described in connection with FIGS. 2 and 3, drive member 274 is driven from its outwardly disposed drive ears or tabs 160 and 162 which extend through slots, one of which is shown at 152. Drive member 274 associated with these tabs is shown in FIG. 4 in its initial or home orientation. Note that member 274 is attached to drive tube 272 which is slidably mounted over support tube 240. As drive member 274 is driven axially forwardly, the five pursing cables pass through it via five channels. One such channel is stylistically represented in the figure at 276 (see also, FIG. 7).

Looking at FIGS. 5-7 drive tube or component 272 as well as the five capture component cables seen in FIG. 7 at 250-254 extend inwardly through both capture stop component 172 and a safety stop component 282. Drive member 274 is shown just approaching capture stop 172 in FIG. 5. In FIG. 6, the member 274 is shown having freely abuttably engaged capture stop 172. Note in this regard that safety stop 282 is positioned slightly axially forwardly of capture stop 172. FIG. 7 additionally reveals the channels 276-280 formed within drive member 274. When in the orientation shown in FIG. 6, the drive member is fully halted and the capture basket profile 268 is essentially fully configured for the recovery of a tissue specimen or target tissue 230. In this orientation in contact with capture stop 172, the drive member 274 functions to create a stall condition at motor component 186 (FIG. 3) which is utilized to indicate completion of capture, halt the movement of the capture component and remove the electrosurgical current application to cables 250-254.

The positive blockage of the movement of drive member 274 functions to provide the motor stall condition signal without imposing undue stress upon the capture component cables. It also functions to accommodate an improved leaf forward region flexibility as described later herein.

Referring to FIG. 8, tip 36 is depicted in conjunction with precursor electrode assembly 214 configured the maneuvering of tip 36 for carrying out the capturing of tissue volumes having a principal effective diametric extent of, for example, extending from about 10 mm to about 20 mm. For a larger effective diameter of capture specimens, the precursor electrodes will have a lengthier cutting surface extent. The electrode assembly 214 incorporates four precursor electrode components arranged in quadrature or cross-shaped symmetrically about instrument axis 24. Three of the elongate, generally L-shaped precursor electrodes are revealed at 284-286, When electrosurgically excited, the forward surfaces of their stainless steel wire electrodes function to support a cutting arc. Those forward precursor electrode components are, in turn, located just forwardly of the truncated cone-shaped protective tip 216. Their excitation is carried out by, for example, depression of footswitch 98a or button switch 63. When so excited, the precursor electrodes permit a facile positioning of the tip 36 into confronting adjacency with a target tissue volume, again symbolically represented at 230. Mounted rearwardly of the tip component 216 are polymeric tip components 290 and 292 which function to provide a ramp structure through which the leafs of the capture component may extend. In this regard, leaf 300 with an associated cable guiding polymeric sheath 400 is seen in its retracted position. When urged forwardly by drive tube 272 these leafs will slidably extend forwardly and at an attack angle of about 45°. The locus of travel of the leafs defining a capture in cage is represented somewhat symbolically in phantom at 268.

The structure of the cannula or support assembly 22, looking inboard from support component 32 at the forward region 34 is seen to include capture component leafs, two of which are represented at 300 and 300. Next inwardly inboard is the stainless steel support tube 240 which has been described as being mounted rearwardly of bulkhead 242 (FIG. 4) and extends forwardly through cannula or support component 32 to a flared region 306 engaging polymeric tip component 290. This flaring is found to be helpful in permitting the support tube to overcome forces resulting from the rather substantial forwardly directed forces occurring during forward deployment of the capture component leafs and cables. Note additionally, that the somewhat annular space between the wall of cannula or support component 32 and the support tube 240 provides an evacuation system transfer channel diverting elevated temperature fluid. That transfer channel is represented at 308. Channel 308 extends from the intake ports 38 to suction manifold 28 and its associated evacuation outlet 170 (FIG. 4).

Located inside support tube 240 is the electrosurgical precursor electrode tube 244 which extends to the chamber 246 (FIG. 4) at the rearward end of housing 130 for purposes of both support and receiving electrosurgical cutting energy transmitted through electrical contact 146. Tube 244 is shown to be electrically insulated from support tube 240 by a polymeric (polyolefin) shrink-wrap 310.

The precursor electrodes are mounted as a subassembly of four stainless steel electrode wires having the noted generally elongate L-shape as seen, in particular, at 284 and 285 in the instant figure. Elongate components of the precursor electrodes, for example, as identified at 312 and 314 with respect to electrodes 284 and 285, extend into a subassembly tube 316. Four such electrode assemblies are crimped inside of this tube 316 and that also, in turn, is crimped within the forward portion of the precursor electrode tube 244.

In general, within about three seconds following the commencement of the electrosurgical cutting procedure with either the precursor electrodes or the capture component, heat released, for example, from the arc generated steam which condenses within the transfer channel 308 will result in a latent heat of vaporization within that channel which will, in turn, elevate the temperature of the external surface of the wall of cannula or support component 32. This surface heat phenomenon is seen to be accommodated for by utilization of a thermally insulating sheath represented generally at 318 located at the earlier described enlarged central region 218. Sheath 318 comprises a stainless steel tube 320 having forward and rearward standoffs which are configured by rolling the cylindrical end of the tube. The forward standoff is shown at 322. With this construction, an annular air gap or air layer 324 is defined which provides thermal insulation. The figure further reveals that extending over the cannula or support component assembly 22 is an electrically insulative polyolefin shrink-wrap or shrink tube 326. Polyolefin wrap 326 has a thickness of about 0.003 inch. Note that it extends to a forward terminus 328. The gap provided at air layer 324 by the tube 320 is about a 0.017 inch annulus-shaped spacing.

Referring to FIG. 9 the capture component which is retained within the internal structure of support component 32 prior to its deployment is represented in general at 340 at a stage of its fabrication prior to the attachment of pursing cables. Component 340 is formed of five elongate thin leafs each of which extend forwardly from a base portion as represented generally at 342 to a tip region represented generally at 344. Each leaf is configured with two components, a thin resilient drive component and an electrically insulative polymeric guide component. The drive components are formed of a type 304 stainless steel having a thickness of about 0.003 inch. However, that thickness may range from about 0.0025 inch to about 0.005 inch. Such drive components are formed by chemically milling flat stainless steel sheet stock. Looking to FIG. 10 the chemical milling is seen to provide each of the leafs 300-304 with a respective base region 350-354 having a width $W_B$ (FIG. 15) defined between leaf edges of about 0.08 inch. These edges extend parallel to each leaf axis as at 356 and are defined, in part, by chemically milled bend lines or troughs as are identified in FIG. 10 at 358-362. Each base region extends with width $W_B$ to a guide commencement location represented generally at 364 at which position each leaf is configured with an integrally formed elongate guide support region shown respectively at 370-374. Each region 370-374 is formed with one or more serrated edges shown respectively at 376-380. Regions 370-374 further extend to an integrally formed reinforcing aperture as shown respectively at 382-386. Looking additionally to FIG. 14, the tip region of guide support region 370 is revealed in enlarged fashion.

Each of these guide support regions has a full width, $W_F$ of about 0.060 inch and the serrated edge 376 is configured with rearwardly angled points, one of which is revealed at 388 which are formed by indentations to establish a minimum region width, $W_N$ less than the full-width $W_F$. From a structural standpoint, the effective widths of the region 370 will lie somewhere between the value $W_N$ and $W_F$. Note, additionally in the figure, that a chemically milled bend line or indentation 390 extends along the inwardly exposed edge of protective aperture 382. Returning to FIG. 10, with the combination of base regions 350-354 and the corresponding guide support regions 370-374, oppositely disposed shoulders are evolved at the guide commencement location 364. One such shoulder is identified at 392 in conjunction with leaf 304. With the dimensions, $W_B$ and $W_F$ as given above, each shoulder will have a widthwise extent of about 0.010 inch.

FIG. 9 reveals that each guide support region 370-374 is inserted within a cable guide. In this regard, cable guides 400, 401 and 404 are seen mounted with respective leafs 300-301 and 304. Looking to FIGS. 11 and 12, cable guide 400 is seen to be formed as an elongate polymeric extrusion having a coupling portion 406 and an integrally formed guide channel as at 408. Coupling portion 406 is seen to be formed having a receiving slot 410 which is dimensioned to receive guide support region 370 of leaf 300. Thus configured, the coupling portion 406 performs in the manner of a sheath surmounting the guide support region 370. The coupling portion additionally is seen exhibiting a widthwise dimension, $W_G$ which corresponds with the width, $W_B$ of the base regions 350-354 (FIG. 15. Accordingly, the outwardly extending rearward end surface as seen at 414 in FIG. 11 of each of the cable guide components will structurally nest against the shoulders as described at 392 in connection with FIG. 10 when inserted over the guide support regions as at 370-374. FIG. 12 further reveals that the guide channel 408 is formed as a single enclosed conduit 414 having an internal diameter of about 0.015 inch. That diameter is sufficient to receive two of the nineteen strand stainless steel cables which have a nominal diameter of about 0.006 inch.

Referring to FIG. 16-18 the completed tip region of leaf 300 is revealed. Note in the figures, that the protective aperture 382 has been bent upwardly at a right angle such that its opening is in alignment with guide channel 414. Thus, protective aperture 382 cooperates with channel 414 to define a guide outlet as represented generally at 416 in connection with leaf 300. Note that the outlets as at 416 are at the very tip of each leaf. The serrated edge 376 of the guide support region 370 is configured such that the developed points as at 388 will engage the internal surface of receiving slot 410 under conditions wherein the capture component is drawn from an extended orientation back into cannula or support 32. This maneuver is carried out in the course of testing during assembly of the instrument 12. On the other hand, where the capture component 340 is driven outwardly to carry out a capture maneuver, then the shoulders as described at 392 in FIG. 10 will engage the rearward end surface as described at 412 in FIG. 11 in a compressive manner to urge it forwardly as a unit with its associated base and guide support region.

The cable assembly employed with capture component 340 is comprised of five cables. These cables extend from connection with terminator component 248 (FIGS. 4 and 5) through the cannula or support member 32 to enter the guide channel of a given leaf whereupon it exits from the guide outlet and is introduced into the guide outlet of a next adjacent leaf, whereupon it extends through the associated channel to a connection located rearwardly of the guide commencement location. Connection is made by fashioning an enlargement such as a knot or weld ball at the end of the cable. That cable terminus then is inserted through a connector slot. Looking to FIG. 15, a cable 420 is seen extending into guide channel 408.

That cable will exit from guide outlet 416 and reenter the guide outlet of a next adjacent leaf. In this regard, FIG. 15 shows the cable 424 from a next adjacent leaf as having entered guide outlet 416 and extends to an enlargement 426 at its terminus which has been inserted into a keyway shaped slot 428. Each leaf of the capture component 340 is configured in the same manner. FIG. 19 reveals cables 420 and 424 within the channel 414 of guide channel 408. While two side by side channels may be contemplated in place of the singular channel 414, because of the very minuscule size of cable guides as at 400, fabrication complexities favor the utilization of a single channel.

Inasmuch as the integrally associated cable guide components and coupling portions 400-404 are formed of polytetrafluoroethylene (Teflon) the surfaces of the leaf structures will exhibit less friction with respect to the instrument guidance features as they emerge from the forward region 34 of instrument 12. Also, since the forwardly disposed stainless steel guide support region of each leaf is formed with a diminished effective width having a value between $W_N$ and $W_F$ (FIG. 14) enclosed within a polymeric cable guide, an enhanced flexure at the tip region is provided. That enhanced flexure promotes a steep angle of attack during the capture component pursing activity. Capture stop 172 (FIG. 6) prohibits any tendency of the leaf tip regions to be distorted at full capture by the tensioned cables 420-424.

Figure 20:
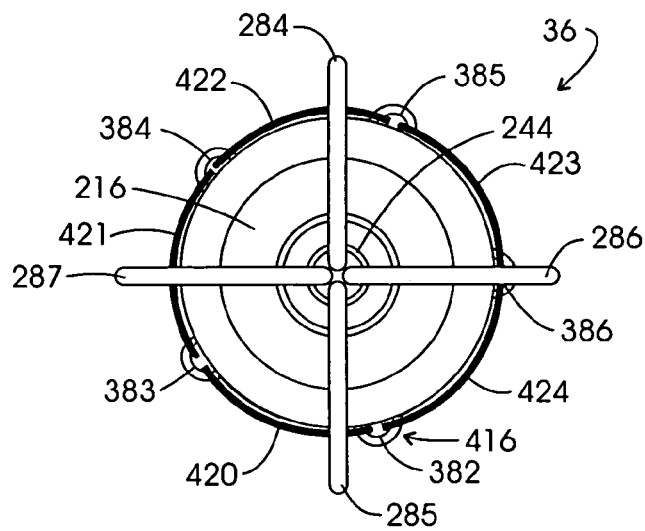
FIG. 20 is a front view of the disposable component shown in FIGS. 4 and 5 illustrating the capture component in its initial orientation.

Referring to FIG. 20 a front view of tip 36 is presented showing the orientation of the capture component when in an initial position essentially retained within the cannula or support component 32. In the figure, cable 420 is shown emerging through protective aperture 382 to enter the guide outlet represented by protective aperture 383 of the next adjacent leaf. Correspondingly, cable 421 emerges from that guide outlet to extend within the guide outlet represented by protective aperture 384 of the next adjacent leaf. Cable 422 emerges from the guide outlet represented at protective aperture 384 to enter the guide outlet represented by protective aperture 385 of a next adjacent leaf. A cable 423 is seen emerging from the guide outlet represented at protective aperture 385 to enter the guide outlet represented at protective aperture 386 and, finally, earlier described cable 424 emerges from the guide outlet represented at protective aperture 386 to enter the guide outlet 416 represented at protective aperture 382.

Figure 21:
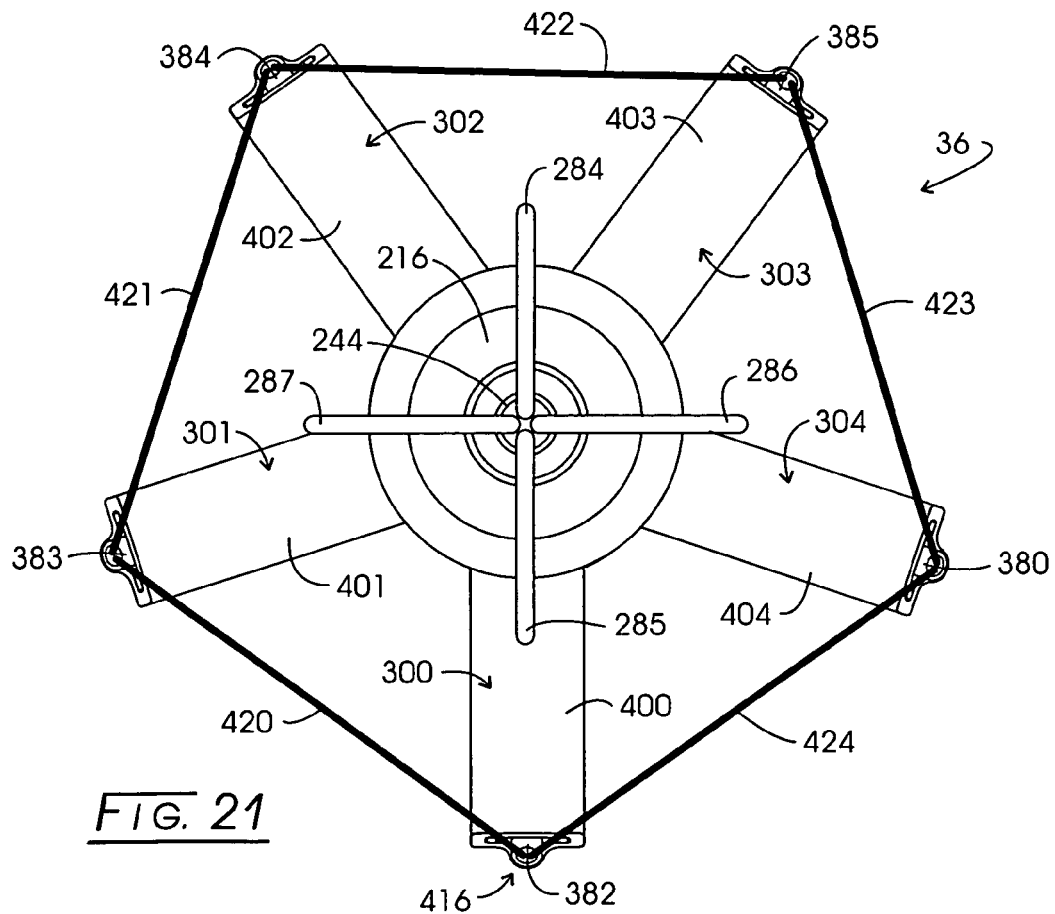
FIG. 21 is a front view of the disposable component shown in FIGS. 4 and 5 illustrating the orientation of the capture component leafs as they approach their maximum diametric extent.

Looking to FIG. 21 the orientation of the capture component is illustrated as it extends about one half of the available total axial distance from the instrument forward region 34. Terminator component 248 will have engaged spring 270 and will have ceased its forward motion by virtue of the blockage posed by stop collar 266. As described in connection with FIG. 6, drive component 276 will continue to be driven until freely abuttably engaging the rearwardly disposed surface of capture stop 172. At this point in the procedure, the capture will have been complete and motor 186 of motor assembly 180 will stall to provide a control system recognizable spike which terminates the capture activity, de-energizing the cutting energy supplied to the pursing cable assembly. The procedure is completed by removal of the instrument with its captured tissue specimen from the patient's body. Additionally, motor assembly 180 reverses to return the yoke 210 to its home position as illustrated in FIG. 3. In this regard, it may be recalled that the yoke generally is in freely abutting drive relationship with the ears 160 and 162 of drive member 274. Accordingly, drive member 274 remains in its forward orientation during this procedure ending activity.

Since certain changes may be made in the above-described apparatus without departing from the scope of the invention herein involved, it is intended that all matter contained in the description thereof or shown in the accompanying drawings shall be interpreted as illustrative and not in a limiting sense.

The invention claimed is:

1. Apparatus for electrosurgically cutting about a tissue volume, comprising:
   a support member having an internal channel and extending to a forward region;
   a tissue capture component positioned within said interior channel, having a leaf assembly comprising a plurality of elongate thin leafs extending forwardly from a base portion to a leaf tip region, a said leaf having a resilient drive component extending along a leaf axis from said base portion to a tip region, and an electrically insulative flexible leaf cable guide component having one or more guide channels deposed parallel with said leaf axis and extending to a guide outlet, and an integrally formed coupling portion mounted with said drive component, a said guide channel extending from said tip region along said drive component to a guide commencement location, said leaf assembly being moveable to deploy outwardly from said support member forward region, said capture component having a pursing cable assembly extending through a said cable guide component guide channel and said guide outlet, electrosurgically energizable and deployable with each said leaf tip region to define an electrosurgical cutting arc of initially expanding extent and subsequent pursively contracting extent;
   a drive assembly engageable with said leaf assembly base portion and said pursing cable assembly and actuable to move said leaf assembly to deploy outwardly from said support member while effecting said deployment of said pursing cable assembly; and
   a control assembly drivably engageable with said drive assembly to effect said actuation thereof and having a terminal electrically coupled with said cable assembly to effect the electrosurgical energization thereof.

2. The apparatus of claim 1 in which:
   said leaf drive component is formed of a resilient metal having a first width at said base portion extending at least to said guide commencement location; and
   said leaf cable guide component is formed of polymeric material.

3. The apparatus of claim 2 in which:
   said leaf cable guide component coupling portion is configured as a sheath surmounting said drive component.

4. The apparatus of claim 3 in which:
   said leaf drive component first width is defined between oppositely disposed edges extending from said base portion to said guide commencement location, and is configured having a second full width less than said first width extending from said guide commencement location to said tip region and defining with said first width oppositely disposed shoulders at said guide commencement location; and
   said leaf cable guide coupling portion is configured having oppositely disposed rearward end surfaces at said guide commencement location extending in abuttable support before said oppositely disposed shoulders.

5. The apparatus of claim 3 in which:
   said leaf drive component is configured having at least one serrated edge with rearwardly directed points engageable with said sheath configured to engage said leaf cable guide component coupling portion when said leafs are moved rearwardly from a deployed orientation toward said support member.

6. The apparatus of claim 4 in which:
   said leaf drive component first width is about 0.080 inch; and
   said leaf drive component second full width is about 0.060 inch.

7. The apparatus of claim 6 in which:
   each said leaf cable guide coupling portion oppositely disposed rearward end surface has a widthwise extent of about 0.010 inch.

8. The apparatus of claim 2 in which:
   said leaf cable guide component has one said guide channel configured to surround one or more cables of said pursing cable assembly between said guide outlet and said guide commencement location.

9. The apparatus of claim 8 in which:
   said guide channel exhibits an internal diametric extent of about 0.015 inch.

10. The apparatus of claim 2 in which:
    said leaf cable guide component polymeric material is polytetrafluoroethylene.

11. The apparatus of claim 1 in which:
    said leaf cable guide component is formed of polymeric material; and
    each said guide channel is reinforced in the vicinity of said guide outlet to an extent effective to avoid damage occasioned during the deployment of said cable assembly.

12. The apparatus of claim 11 in which:
    said leaf resilient drive component is formed of metal and is configured to define a protective aperture extending across said guide outlet at said tip region.

\* \* \* \* \*